United States Patent [19]

Geil

[11] Patent Number: 4,632,108

[45] Date of Patent: Dec. 30, 1986

[54] TUBE AND MATERIAL FOR USE IN LASER SURGERY

[75] Inventor: James A. Geil, St. John, Mo.

[73] Assignee: Sherwood Medical Company, St. Louis, Mo.

[21] Appl. No.: 703,964

[22] Filed: Feb. 21, 1985

[51] Int. Cl.⁴ .......................... A61M 16/00; A62B 9/06
[52] U.S. Cl. .............................. 128/207.14; 128/207.15
[58] Field of Search ...................... 128/207.14, 207.15, 128/207.16, 132 R, 303.1, 395–398; 523/200, 216, 217, 223; 524/403, 441, 586

[56] References Cited

U.S. PATENT DOCUMENTS

| | | | |
|---|---|---|---|
| 3,070,132 | 12/1962 | Sheridan | 138/118 |
| 4,011,360 | 3/1977 | Walsh | 523/217 |
| 4,327,720 | 5/1982 | Bronson et al. | 128/207.15 |
| 4,375,811 | 3/1983 | Sabbota et al. | 604/97 |
| 4,378,796 | 4/1983 | Milhaud | 128/207.15 |
| 4,489,722 | 12/1984 | Ferraro et al. | 128/207.15 |
| 4,520,814 | 6/1985 | Weeks | 128/132 R |
| 4,558,093 | 12/1985 | Hatzenbuhler et al. | 604/21 |

FOREIGN PATENT DOCUMENTS

| | | | |
|---|---|---|---|
| 6092959 | 7/1981 | Japan | 523/217 |
| 7053551 | 3/1982 | Japan | 523/217 |
| 8089645 | 5/1983 | Japan | 523/217 |
| 8089646 | 5/1983 | Japan | 523/217 |
| 8089647 | 5/1983 | Japan | 523/217 |

Primary Examiner—C. Fred Rosenbaum
Assistant Examiner—Jerome R. Smith, Jr.
Attorney, Agent, or Firm—Stanley N. Garber; Andrew J. Beck; William R. O'Meara

[57] ABSTRACT

A flexible tubular assembly has a distal end disposed within the trachea of a patient and a proximal end outside the body of the patient. An inflatable balloon carried on the distal end of tubular assembly can be inflated into sealing contact with the trachea. A first conduit in the tubular assembly conveys anesthesia and ventilation gases through the assembly and a second conduit is used to inflate the balloon. The flexible tubular assembly includes a polymeric matrix having a reflective filler embedded therein. The filler includes finely divided particles having a metallic surface coating which is reflective to infrared laser radiation. The tubular assembly also includes a smoke removal lumen with an opening proximal the balloon to remove smoke generated during laser surgery.

5 Claims, 3 Drawing Figures

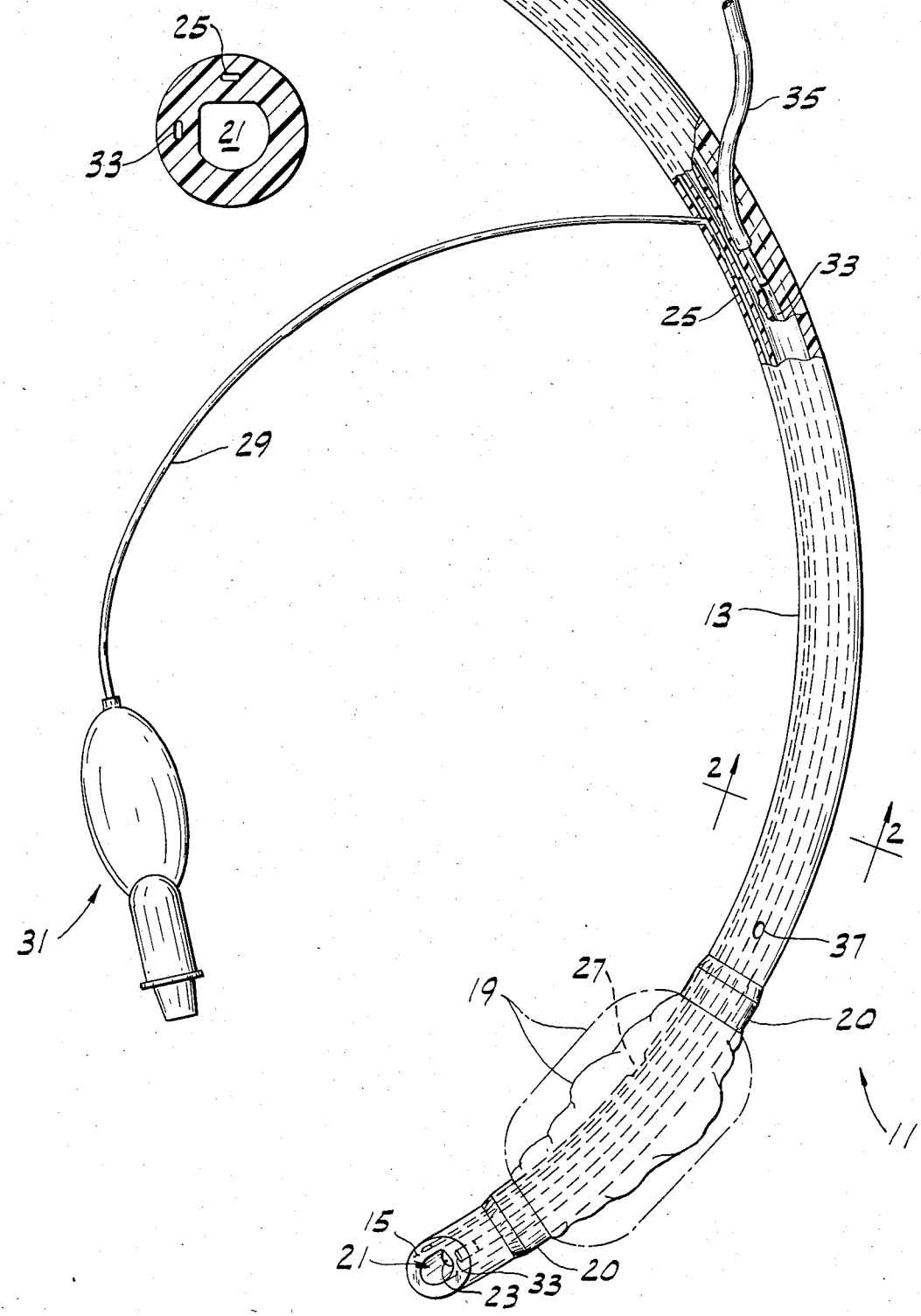

TUBE AND MATERIAL FOR USE IN LASER SURGERY

BACKGROUND OF THE INVENTION

This invention relates generally to laser surgery, and more particularly to materials and endotracheal tubes useful in such surgery.

Tracheal tubes are used during surgical procedures to provide ventilation and anesthesia for the patient. The distal ends of these tubes are inserted into the lower portions of the trachea and have a balloon disposed at the distal end which may be inflated from outside the patient through an auxiliary lumen, so as to provide an effective leak resistant seal between the tube and the trachea. Such tubes, however, in the case of laser surgery of the throat, present certain difficulties. For example, materials such as polyvinyl chloride (PVC) that are normally used to make endotracheal tubes absorb infrared energy from the laser if the laser beam happens to strike the tube. As a result, the laser can in effect burn a hole through the tube with potentially serious consequences for the patient. Not only does the tube convey high concentrations of oxygen, but in many cases the gas flowing through the main lumen of the endotracheal tube may be another highly flammable gas. A hole burned through the tube wall exposing the oxygen or flammable anesthestic gas can cause ignition of the tube while in the patient's trachea with obvious catastrophic results.

Of course a material that would resist penetration by a laser beam could find additional uses for shielding during laser surgery on other parts of the body.

As a result of the disadvantages mentioned above, endotracheal tubes have previously been protected by a helical winding of a strip of material such as aluminum which reflects the infrared energy of the laser. This protects the tube, but is believed to drastically affect the safety and flexibility of the tube. Endotracheal tubes have also been made of metal. However, this results in rigid tubes which traumatize the patient's respiratory tract. In addition, laser beams can reflect off the metallic surface of such a tube onto healthy tissues, which results in unnecessary trauma to the patient.

Other tubes, such as that shown in U.S. Pat. No. 4,378,796, have been proposed to address these disadvantages. The tube of the '796 patent includes a dispersion of finely divided metallic powder such as aluminum, silver, or gold which allegedly absorb and reflect energy received from the impact of the laser beam. It is stated to be advantageous if the whole of the endotracheal tube comprises such a metallic dispersion, so that its resistance to the infrared energy of the laser beam is improved. An example of such a tube is given in the '796 patent in which the tube itself is of silicone containing 1% by weight aluminum powder.

An endotracheal tube made of an oxide of a metal for the same purpose is described in U.S. Pat. No. 4,375,811.

During laser surgery, particularly in the area of the trachea, the space above the balloon of the endotracheal tube can become filled with smoke due to the action of the laser on the tissues. This, of course, complicates the surgeon's job. The aforementioned U.S. Pat. No. 4,378,796 attempts to address this problem by providing an auxiliary lumen with an opening on the side of the endotracheal tube proximal to the balloon through which lumen an inert gas, such as nitrogen, is passed to sweep the smoke out of the upper part of the trachea.

SUMMARY OF THE INVENTION

Among the various objects and features of the present invention may be noted the provision of a material for use in laser surgery which resists damage from inadvertent strikes from a laser beam; the provision of an endotracheal tube made of such material; the provision of such an endotracheal tube which improves visibility during laser surgery; the provision of such an endotracheal tube which is more resistant to laser radiation than previously available flexible tubes; the provision of such an endotracheal tube which does not significantly reflect laser radiation onto healthy tissue; and the provision of such an endotracheal tube which is relatively economical in manufacture. Other aspects and features of the present invention will be in part apparent and in part pointed out hereinafter.

Briefly, the laser resistant medical material of the present invention includes a polymeric matrix generally opaque to laser radiation of a frequency used in laser surgery. The matrix is generally nonreflective to the laser radiation and has a relatively poor thermal conductivity. A reflective filler is embedded in the polymeric matrix to retard the laser radiation from burning through the matrix. The filler includes finely divided particles, each having a metallic surface coating which is reflective to the laser radiation.

A laser resistant endotracheal tube of the present invention includes a flexible tubular assembly having a distal end which in operation is disposed within the trachea of a patient and a proximal end which in operation is disposed outside the body of the patient. An inflatable balloon is carried on the distal end of the tubular assembly and is adapted to be inflated into sealing contact with the trachea. A first conduit in the tubular assembly conveys anesthesia and ventilation gases through the assembly and a second conduit in the tubular assembly is used in inflating the balloon. The tubular assembly includes a polymeric matrix having a reflective filler embedded therein, the filler including finely divided particles each having a metallic surface coating.

A ventilation system of the present invention for use during laser surgery includes a flexible tubular assembly havng a distal end which in operation is disposed within the trachea of a patient and a proximal end which in operation is disposed outside the body of the patient. An inflatable balloon is carried on the distal end of the tubular assembly and is adapted to be inflated into sealing contact with the trachea. A first conduit in the tubular assembly conveys anesthesia and ventilation gases through the assembly. A valve and tube are provided for inflating the balloon. A second conduit in the tubular assembly is provided for removing smoke from the space proximal the balloon to the exterior of the body of the patient, the second conduit having a first opening proximal the balloon and a second opening proximal the first opening. A vacuum source is connected to the second opening of the second conduit for withdrawing the smoke through the second conduit.

BRIEF DESCRIPTION OF THE DRAWING

FIG. 1 is a side elevation of an endotracheal tube of the present invention with parts broken away for clarity;

FIG. 2 is a section taken generally along line 2—2 of FIG. 1; and

Similar reference characters indicates similar parts throughout the several views of the drawings.

DESCRIPTION OF THE PREFERRED EMBODIMENT

Figure 3:
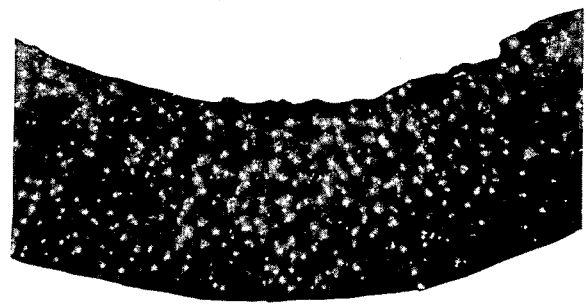
FIG. 3 is a photomicrograph illustrating the structure of the material of the endotracheal tube of FIG. 1.

Turning now to the drawings, an endotracheal tube 11 of the present invention includes a flexible tubular assembly 13 having a tapered distal end 15 which in operation is disposed within the trachea of a patient and a proximal end 17 which in operation is disposed outside the body of the patient. An inflatable balloon 19 is carried on and suitably secured to the distal end of tubular assembly 13 and is adapted to be inflated from the position shown in solid lines in FIG. 1 to the position shown in dashed lines in FIG. 1 in which it is in sealing contact with the trachea of the patient. Specifically, balloon 19 can be a conventional inflatable balloon bonded with room temperature vulcanizing silicone (RTV) in the areas indicated by reference numeral 20, which areas are tapered or blended smoothly to the tube or tubular assembly 13 as indicated for the entire circumference of the tubular assembly.

A first conduit 21 extends from the distal to the proximal ends of tubular assembly 13 for conveying anesthesia and ventilation gases through the assembly. An auxiliary eye 23 is provided in the side wall of the distal end of tubular assembly 13 to provide communication between the exterior of the tubular assembly and conduit 21 in case the distal end of the conduit becomes plugged during use and to provide for a better distribution of gas to both lungs. The proximal end of conduit 21 in operation is connected to a source of oxygen, other ventilation gas, and/or anesthesia gas, not shown. A secondary lumen or conduit 25 is provided for use in inflating balloon 19 from the position shown in solid lines in FIG. 1 to the position shown in dashed lines. Lumen 25 is plugged at the distal end of tubular assembly 13 by RTV and communicates with the interior of balloon 19 through an opening 27 through the sidewall of tubular assembly 13. An inflation tube 29 is suitably secured by RTV into lumen 25 generally in the vicinity of the proximal end of tubular assembly 13. Inflation tube 29 has an open interior lumen which is in fluid communication with the lumen 25 of the tubular assembly distal to the point of attachment of tube 29 to the tubular assembly. Since the extreme distal end of lumen 25 is plugged with RTV, tube 29 and the distal approximately two thirds of lumen 25 form a generally air tight path for the passage of inflation fluid (air) to and from balloon 19. The other end of inflation tube 29 is connected to an inflation valve system 31 of conventional design which is adapted to receive a syringe for injection of inflating fluid. As an example, balloon 19 may be inflated to the position shown in dashed lines by a suitable volume of air.

Tubular assembly 13 has a third lumen or conduit 33, which like lumens 21 and 25, are integrally formed therein. Lumen 33, like lumen 25, is plugged with RTV at the distal end of tubular assembly 13 and is effectively terminated (although the lumen itself extends through to the proximal end of the tube) at the point in the general vicinity of the proximal end of the tubular assembly where a smoke removal tube 35 is inserted into lumen 33. Like balloon inflation tube 29, the smoke removal tube 35 is bonded in place by RTV. Just proximal the balloon 19, an opening 37 from the exterior of tubular assembly 13 to the interior of lumen 33 is provided so that smoke occurring above balloon 19 can be removed through lumen 33. In particular, the proximal end of smoke removal tube 35 is suitably connected by an adapter 39 to a vacuum source 41. It has been found that a vacuum of 120 to 200 millimeters of mercury can give a flow rate of 1 to 3 liters per minute through smoke removal lumen 35, which flow rate is believed to be sufficient to remove smoke resulting from the laser surgery at a steady rate. Of course smoke removal lumen 37 could also be used for removal of secretions from the area proximal to balloon 19.

Turning to FIG. 2, it is seen that tubular assembly 13 is generally circular in cross-section with lumens 21, 25, and 33 formed integrally therein.

Turning to FIG. 3, there is shown a microphotograph of the wall of endotracheal tube 11 illustrating the material of the present invention. Specifically, the material includes a common medical grade silicone matrix in which is embedded a reflective filler. Silicone is generally opaque to the IR (infrared) laser radiation used in laser surgery and is generally non-reflective to that laser radiation. Moreover, it has relatively poor thermal conductivity. As a result, when the laser beam inadvertently strikes a silicone tube, it melts or burns a hole through the silicone from the exterior to the interior of the tube. Since relatively explosive gases sometimes flow through the tube, it is quite hazardous when the laser beam accidently burns through the wall of the endotracheal tube. It has been found, however, that the tube can be made resistant to laser radiation by embedding finely divided particles in the silicone matrix, each particle having a metallic surface coating which is reflective to the laser radiation. More specifically, it has been found that silver coated glass beads make an excellent filler material, which can be coextruded with the silicone to form tubular assembly 13. For example, 75 micron glass spheres were plated with 99% pure silver. These silver coated glass spheres were then coextruded with common medical grade of silicone to form a tubular assembly 13. The density of the silver coated glass spheres was selected to be high enough so that the particles overlapped to produce beam interference. As an example, 35% by weight of glass spheres along with 4% by weight silver plated on the spheres provided an endotracheal tube with excellent laser resisting characteristics. Of course, the glass spheres could be coated with other materials which are reflective to infrared radiation, such as aluminum or gold. And the actual size of the glass spheres is not a critical feature of the present invention. It is believed that the silver coated glass spheres provide the laser resisting characteristics of tube 11 in several cooperating ways. For one, the spherical shape of the glass spheres results in any incident laser radiation being defocused into the surrounding matrix, thereby reducing the power levels to which the silicone is subjected. This slows the burning or melting process. In addition, the thermal conductivity of the silver coating results in the heat being deposited by the laser being distributed around the glass sphere and even from sphere to sphere, again resulting in reduced burning or melting. Finally, the mere fact that the silver reflects the incident laser radiation from particle to particle results in the laser beam being forced to burn through a longer path of material before it burns through to the main lumen 21.

In view of the above, it is believed that the various aspects and features of the invention are achieved and other advantageous results attained. As various changes could be made in the tube and material without departing from the scope of the invention, it is intended that all matter contained in the above description or shown in accompanying drawing shall be interpreted as illustrative and not in a limiting sense.

What is claimed is:

1. A flexible, laser-resistant surgical tube for use in connection with laser surgery, said tube being defined by a tubular wall and comprising a polymeric materix generally non-reflective to laser radiation and having relatively poor thermal conductivity, said polymeric matrix having a laser-reflective filler embedded therein to retard laser radiation from buring through the polymeric matrix of the surgical tube, said filler constituting not more than about 35% by weight of said matrix and comprising spaced, finely divided particles uniformly distributed throughout said matrix, the density of said particles in said matrix being sufficient such that the particles overlap when viewed from the direction of the source of laser radiation, said particles including a dielectric core of a geometric shape to defocus, diffuse and disperse laser radiation impinging on the surface thereof, said particles further including a laser-reflective metallic surface coating encasing said core whereby said metallic coated particles retard burning of the matrix of said surgical tube by reflecting laser radiation and, by virtue of the shape of said particles, by defocusing, diffusing and dispersing laser radiation through out the adjacent matrix of the surgical tube and distributing heat therefrom about the periphery of said particles to the matrix adjacent thereto.

2. A flexible, laser-resistant surgical tube according to claim 1 wherein said particles are spherical in shape, said dielectric cores of said particles comprising glass spheres and said laser-reflective metallic surface coating about said cores comprising a noble metal coating about the periphery of said glass spheres.

3. A flexible laser-resistant surgical tube according to claim 2 wherein said polymeric matrix is silicone, and said metallic coating is silver and constitutes about 4% by weight of the filler.

4. A flexible laser-resistant surgical tube according to claim 3 wherein said tube includes a proximal and a distal end, said distal end being adapted to be disposed within the trachea of a patient and said proximal end thereof being adapted to be disposed outside of the body of the patient; an inflatable balloon fixed on said distal end, said balloon being adapted to be inflated into sealing contact with the patient's trachea, said tubular wall defining a first conduit means in said tube of a relatively large diameter for conveying anesthesia and ventilating gases therethrough and a second conduit means in said tubular wall of a relatively smaller diameter in fluid communication with the interior of said balloon for inflating said balloon.

5. A flexible laser-resistant surgical tube according to claim 4 further comprising third conduit means of a smaller diameter than said first conduit means, said third conduit means having an inlet through said tubular wall adjacent the proximal end of said balloon and an outlet adjacent said proximal end of said tube, said outlet being adapted to be connected to a source of vacuum for removing fluids from about the outer periphery of said tubular wall adjacent said proximal end of said balloon.

* * * * *